United States Patent
Wanner et al.

(10) Patent No.: US 7,074,334 B2
(45) Date of Patent: Jul. 11, 2006

(54) METHOD FOR DETERMINING THE BINDING BEHAVIOR OF LIGANDS WHICH SPECIFICALLY BIND TO TARGET MOLECULES

(76) Inventors: Klaus Wanner, Kreillerstrasse 122, D-81825 Munich (DE); Georg Höfner, Am Olivberg 44, D-83607 Holzkirchen (DE); Wolf Bertling, Meisenweg 22, D-91056 Erlangen (DE)

( * ) Notice: Subject to any disclaimer, the term of this patent is extended or adjusted under 35 U.S.C. 154(b) by 403 days.

(21) Appl. No.: 10/478,025

(22) PCT Filed: May 21, 2002

(86) PCT No.: PCT/EP02/05543

§ 371 (c)(1),
(2), (4) Date: Nov. 15, 2003

(87) PCT Pub. No.: WO02/095403

PCT Pub. Date: Nov. 28, 2002

(65) Prior Publication Data

US 2004/0232077 A1 Nov. 25, 2004

(30) Foreign Application Priority Data

May 23, 2001 (DE) ................. 101 25 258

(51) Int. Cl.
*B01D 15/08* (2006.01)
(52) U.S. Cl. .............. 210/656; 210/659; 210/198.2; 435/7.1; 436/517; 436/518
(58) Field of Classification Search ............... 435/7.1; 436/517, 518; 210/635, 656, 659, 143, 198.2
See application file for complete search history.

(56) References Cited

U.S. PATENT DOCUMENTS

| | | | |
|---|---|---|---|
| 5,494,792 A | 2/1996 | Kamboj et al. | |
| 5,573,922 A | 11/1996 | Hoess et al. | |
| 5,679,526 A | 10/1997 | Buechler et al. | |
| 5,770,457 A | 6/1998 | Stocker et al. | |
| 5,872,015 A | 2/1999 | Venton et al. | |
| 5,891,742 A | 4/1999 | Dollinger et al. | |
| 5,935,442 A | 8/1999 | Lihme et al. | |
| 5,959,297 A | 9/1999 | Weinberg et al. | |
| 5,986,076 A * | 11/1999 | Rothschild et al. | 536/22.1 |
| 6,005,083 A * | 12/1999 | Kasina | 534/10 |
| 6,010,861 A | 1/2000 | Blume | |
| 6,022,694 A | 2/2000 | Radziejewski et al. | |
| 6,043,067 A | 3/2000 | Lihme et al. | |
| 6,143,574 A | 11/2000 | Karlsson et al. | |

(Continued)

FOREIGN PATENT DOCUMENTS

DE    3541611 A1    5/1987

(Continued)

OTHER PUBLICATIONS

Daniel et al., International Journal of Mass Spectrometry 216 (2002), pp. 1-27.

(Continued)

*Primary Examiner*—Ernest G. Therkorn
(74) *Attorney, Agent, or Firm*—Heribert F. Muensterer (57) ABSTRACT

The invention relates to a method for determining the binding behavior of ligands which specifically bind to target molecules at at least one binding site, whereby the markers are present in a native form and the determination of the concentrations K4 and K5 or of the quantities M2 and M1 is carried out by means of mass spectrometry.

33 Claims, 2 Drawing Sheets

U.S. PATENT DOCUMENTS

| | | |
|---|---|---|
| 6,207,861 B1 | 3/2001 | Nash et al. |
| 6,335,155 B1 | 1/2002 | Wells et al. |
| 6,358,692 B1 | 3/2002 | Jindal et al. |
| 6,387,707 B1 * | 5/2002 | Seul et al. .................. 436/164 |
| 6,428,956 B1 | 8/2002 | Crooke et al. |
| 6,432,651 B1 | 8/2002 | Hughes et al. |
| 6,537,760 B1 | 3/2003 | Bergmann et al. |
| 6,627,882 B1 | 9/2003 | Schultz et al. |
| 6,638,725 B1 | 10/2003 | Soya et al. |
| 6,721,665 B1 | 4/2004 | Birnbaum et al. |
| 6,723,235 B1 | 4/2004 | Hindsgaul et al. |
| 2002/0052006 A1 | 5/2002 | Dunayevskiy et al. |
| 2002/0127609 A1 | 9/2002 | Davis et al. |
| 2003/0022393 A1 * | 1/2003 | Seul et al. .................. 436/518 |
| 2003/0138788 A1 | 7/2003 | Kalghatgi et al. |
| 2004/0053424 A1 | 3/2004 | Irth |
| 2004/0232077 A1 * | 11/2004 | Wanner et al. ............... 210/638 |

FOREIGN PATENT DOCUMENTS

| | | |
|---|---|---|
| DE | 19749163 A1 | 5/1999 |
| DE | 19814775 A1 | 10/1999 |
| EP | 0426083 A1 | 5/1991 |
| EP | 0463144 B1 | 1/1992 |
| EP | 0607998 B1 | 7/1994 |
| EP | 1106702 A1 | 6/2001 |
| GB | 2291708 A | 1/1996 |
| WO | WO-83/03306 A1 | 9/1983 |
| WO | WO-92/18866 A1 | 10/1992 |
| WO | WO-96/37777 A1 | 11/1996 |
| WO | WO-97/43301 A2 | 11/1997 |
| WO | WO-98/56028 A1 | 12/1998 |
| WO | WO 98/57172 A1 | 12/1998 |
| WO | WO-99/05309 A1 | 2/1999 |
| WO | WO-99/50669 A1 | 10/1999 |
| WO | WO-00/39585 A1 | 7/2000 |
| WO | WO-00/47999 A1 | 8/2000 |
| WO | WO-00/65353 A1 | 11/2000 |
| WO | WO-00/65354 A1 | 11/2000 |
| WO | WO-00/79260 A1 | 12/2000 |
| WO | WO-01/02865 A1 | 1/2001 |
| WO | WO-01/22078 A1 | 3/2001 |
| WO | WO-01/94943 A2 | 12/2001 |
| WO | WO-02/031491 A2 | 4/2002 |
| WO | WO-02/066135 A1 | 8/2002 |
| WO | WO-02/082066 A1 | 10/2002 |
| WO | WO-02/086168 A1 | 10/2002 |
| WO | WO-03/012398 A1 | 2/2003 |
| WO | WO-03/023839 A1 | 3/2003 |
| WO | WO-03/102222 A2 | 12/2003 |

OTHER PUBLICATIONS

Bronstrup, Top. Curr. Chem. (2003), pp. 283-302.
Van Breemen in Burger's Medicinal Chemistry and Drug Discovery, 6th ed. vol. 1 (2003), Chapter 13, pp. 584-610.
Kassel, Chem. Rev. 2001, 101, pp. 255-267.
Strege, Journal of Chromatography B, 725 (1999), pp. 67-78.
Sussmuth et al., Journal of Chromatography B, 725 (1999), pp. 49-65.
Lenz et al., DDT vol. 5, No. 4 Apr. 2000, pp. 145-156.
Tang et al., Biomed. Chromatogr. 14: pp. 442-449 (2000).
Kaur et al., Journal of Protein Chemistry, vol. 16, No. 5, 1997 pp. 505-511.
Schriemer et al., Angew Chem. 1998, 110, Nr. 24, pp. 3625-3628.
Gu et al., Combinatorial Chemistry & High Throughput Screening, 1999, 2, pp. 353-359.
Van Breemen et al., Anal. Chem. 1997, 69, pp. 2159-2164.
Zhao et al., J. Med. Chem. 1997, 40, pp. 4006-4012.
Nikolic et al., Anal. Chem. 2000, 72, pp. 3853-3859.
Kelly et al., Biochemistry 1996, 35, pp. 11747-11755.
Hogenboom et al., Anal. Chem. 2001, 73, pp. 3816-3823.
Sannes-Lowery et al., trends in analytical chemistry, vol. 19, No. 8, pp. 481-491.
Sannes-Lowery et al., Analytical Biochemistry 280, pp. 264-271 (2000).
Huyer et al., Analytical Biochemistry 258, pp. 19-30 (1998).
Zhang et al., Anal Chem. 2003, 75, pp. 3010-3018.
Wieboldt et al., Anal. Chem. 1997, 69, pp. 1683-1691.
Nedved et al., Anal. Chem. 1996, 68, pp. 4228-4236.
Chu et al., J. Am. Chem. Soc. 1996, 118, pp. 7827-7835.
Zuckermann et al., Proc. Natl. Acad. Sci. USA, 89, pp. 4505-4509, May 1992.
Hsieh et al., Journal of Biomolecular Screening, vol. 3, No. 3, 1998, pp. 189-198.
Wu et al., Chemistry & Biology 1997, vol. 4, No. 9, pp. 653-657.
Cheng et al., J. Am. Chem. Soc. 1995, 117, pp. 8859-8860.
Blom et al., J. Comb. Chem. 1999, 1, pp. 82-90.
Nelson et al., Anal. Chem. 1995, 67, pp. 1153-1158.
Yin et al., Xenobiotica, 2000, vol. 30, No. 2, pp. 141-154.
Gao et al., J. Med. Chem. 1996, 39, pp. 1949-1955.
Hsieh et al., Molecular Diversity, 2(1996), pp. 189-196.
Seifert et al., Fresenius J. Anal. Chem. (1999) 363, pp. 767-770.
Derks et al., Anal. Chem. 2003, 75, pp. 3376-3384.
English Language Abstract (esp@cenet) of DE-19814775.
English Language Abstract (esp@cenet) of DE-19749163.
English Language Abstract (esp@cenet) of DE-3541611.
English Language Abstract (esp@cenet) of EP-0426083.

* cited by examiner

METHOD FOR DETERMINING THE BINDING BEHAVIOR OF LIGANDS WHICH SPECIFICALLY BIND TO TARGET MOLECULES

CROSS-REFERENCE TO RELATED APPLICATIONS

The present application is a U.S. National Stage of International Application No. PCT/EP02/05543, filed May 21, 2002, which claims priority under 35 U.S.C. § 119 of German Patent Application No. 101 25 258.7, filed May 23, 2001.

BACKGROUND OF THE INVENTION

1. Field of the Invention

The invention relates to a method for determining the binding behavior of ligands which specifically bind to target molecules at at least one binding site.

2. Discussion of Background Information

DE 198 14 775 A1 discloses a method for determining the binding constants of dissolved agents and substances on surfaces constituted by amphiphilic molecules. Therein, layers of amphiphilic molecules are bonded to a solid carrier so that a solid-supported membrane is formed. A defined quantity of this solid-supported membrane is contacted with a mobile phase. The mobile phase contains a defined quantity of substances which are to be examined with respect to lipid binding. After an incubation, the solid-supported membranes are separated from the mobile phase. The concentrations of the substances in the mobile phase or the solid-supported membrane are determined. The method can be carried out with solid-supported membranes and substances that are present in different quantity ratios. From the determined concentrations, the binding constant can be calculated.

From WO 99/50669 A1 there is known a method for screening a compound library to determine the relative affinity of a plurality of putative ligands to a target receptor in relation to an indicator compound by means of frontal chromatography. Therein, the target receptors are immobilized on the solid phase of a chromatographic column. The compound library is applied onto the chromatographic column and equilibrated therewith at least partially. Subsequently, the indicator compound is applied and its break through time, i.e., the time until it appears in the effluent of the chromatographic column, is determined by means of mass spectrometry. The break through time of the indicator compound is affected by its affinity, the affinity of ligands present to the target receptor, and the number of target receptors which are not occupied by the ligands. From the change in the break through time in comparison to the known break through time of the indicator compound, it can be determined whether compounds of the compound library have an affinity to the target receptors, and whether this affinity is higher or lower than that of the indicator compound.

A disadvantage of this method is that the target receptors are invariably immobilized. They are not present in the native state, whereby it is possible to only a limited extent to say something about the binding behavior on native target receptors. A further disadvantage of the method is that in kinetic studies, it leads to incorrect results regarding the binding behavior between ligands and the indicator compound. If a ligand and the indicator compound had the same affinities to the target receptor, the affinity of the ligand would be determined as too low if the ligand shows slower binding kinetics relative to the indicator compound. A further disadvantage is that the quantity of the indicator compound which is bound or unbound, respectively, in the binding equilibrium state cannot be determined.

WO 01/22078 A1 relates to a method for the identification of an active chemical substance from a mixture of active and inactive chemical substances, where a target substance is added to the mixture. Complexes formed of the active substance and the target substance are separated from the mixture. For identification, the active chemical substance may be released from the complexes and identified by, for example, mass spectrometry. Alternatively, the active substance may also be identified by comparing a chromatogram or a mass spectrum, respectively, of each of the mixture of active and inactive substances and the mixture after separation of the complex. A disadvantage thereof is that it must be possible to determine each of the substances of the mixture.

WO 97/43301 A2 relates to a method for characterizing the members of a combinatorial library which bind to a certain domain. Therein, the domain is mixed with the members of the combinatorial library to permit a binding of the members to the domain. The formed complexes are separated from the unbound members. The bound members are eluted from the complexes and analyzed by mass spectrometry. Therein, it is possible to elute more weakly bound members separately from more strongly bound members. A disadvantage thereof is that each of the members of the mixture must be determinable by mass spectrometry.

From WO 96/22530 A1 and U.S. Pat. No. 5,891,742 A there is known a method for determining a compound which binds to a target compound from a mixture of compounds. Therein, the target compound is contacted with the mixture of compounds. Unbound compounds are separated from formed complexes of the compounds with the target molecules. The formed complexes are analyzed by mass spectrometry. It is of disadvantage therein that all compounds and complexes, respectively, of the binding assay must be determinable by mass spectrometry.

From WO 00/00823 A1 there is known a method for identifying a ligand which covalently binds to a target molecule. In this method, a target molecule is contacted with several compounds of a substance library. The compound which forms a covalent bond with a chemically reactive group of the target molecule is identified by mass spectrometry. For this purpose, the conjugate formed by the covalent bond may be fragmented. The bound compound may as well be released by cleaving a disulfide bond. For identification, the mass spectroscopic characteristics of the compounds to be determined or of the fragment to be determined, respectively, must be known in this method.

From WO 99/45150 A1 there is known a method for determining the relative binding affinity to a target substance of compounds of a combinatorial mixture. Therein, a first complex of the target substance and a standard compound binding thereto is contacted with the combinatorial mixture of compounds, whereby second complexes are formed from these compounds and the target substance. The mixture is analyzed by mass spectrometry. From the quantity of first and second complexes contained therein, the relative binding affinity can be determined. Also in this assay, it must be possible to analyze all compounds which potentially form complexes with the target molecules, and the complexes formed therefrom, respectively.

From WO 00/47999 A1 there is known a method for screening complex biological samples for a ligand which binds to a target protein. Therein, the target protein is mixed with the complex biological sample and incubated under conditions which permit the formation of complexes of ligands with the target protein. Formed ligand-target protein complexes are separated and caused to dissociate. Released ligands can be analyzed by mass spectrometry following the separation of the target protein. The separation is effected in each case by means of size exclusion processes. Furthermore, WO 00/47999 A1 discloses the use of a reference substance and of a known competitive ligand. The competitive ligand serves to determine whether a ligand binds specifically or non-specifically to the selected target protein. For this purpose, the competitive ligand is mixed with the complex biological sample, the process is carried out as described, and it is determined whether the mass spectroscopic signal of the ligand is affected by the presence of the competitive ligand. The method discloses a comparison of the binding assays in the presence and absence of the competitive ligand. However, all bound ligands are invariably determined by mass spectrometry.

Moreover, it is generally known form the prior art to indirectly determine the binding of unlabeled ligands to a target molecule by means of ligands which are labeled with a marker substance. Therein, the unlabeled ligands are incubated with the target molecules together with a defined portion of labeled ligands. The subsequent determination of the quantity of the marker substance which is bound to the target molecules through the labeled ligands allows the determination of the binding behavior of the ligands which are bound to the target molecules.

The methods known in the prior art make it necessary to directly or indirectly quantify either the bound or the unbound ligands. With direct quantification, this may involve a substantial expenditure, depending on the ligand. For quantification, the employed detection system must be calibrated for each of the ligands to be quantified. This is necessary also for ligands of which it is not known whether they show an affinity to the target molecules. The indirect quantification by means of labeled ligands involves substantial expenditure as well. Initially it is necessary to label the ligands with a marker substance so that the labeled ligands still have sufficient affinity to the target molecules. Frequently, various labeling methods with various marker substances must be tested for this purpose. Often, only radioactive marker substances prove to be suitable. Handling these marker substances and the ligands labeled therewith is dangerous, and because of the required safety precautions, it involves substantial expenditure. Furthermore, not every ligand is suitable for labeling by a certain desired method. This may necessitate a search for suitable ligands.

Object of the present invention is the elimination of the disadvantages of the prior art. In particular, there is to be provided a method which makes it possible to determine, with little expenditure, the specific binding behavior of any ligands to any desired target molecules, unaffected to a large extent by the kinetics of the binding of the ligands to the target molecules.

This problem is solved by the features of the claimed invention.

SUMMARY OF THE INVENTION

The present invention provides a method for determining the binding behavior of ligands which bind specifically to target molecules at at least one binding site, which method comprises:

(A) preparing a first mixed phase wherein the ligands are contacted with (i) markers which bind specifically to the target molecules, and (ii) with the target molecules, wherein the ligands are present in a concentration K1, the markers are present in a concentration K2 and the target molecules are present in a concentration K3;

(B) preparing a second mixed phase wherein the markers are contacted with the target molecules;

(C) incubating the first and second mixed phases under identical conditions, which conditions permit a binding of the ligands and the markers to the target molecules, resulting in (a) a quantity M1 of markers GM1 that are bound to target molecules and a concentration K4 of unbound markers in the first mixed phase and (b) a quantity M2 of markers GM2 that are bound to target molecules and a concentration K5 of unbound markers in the second mixed phase;

(D) separating the markers GM1 from the first mixed phase and separating the markers GM2 from the second mixed phase;

(E1) determination of the concentrations K4 and K5, and calculating a concentration K6 from K5, wherein K6 is a concentration of unbound markers in the second mixed phase under the assumption that the markers have been contacted therein in the concentration K2 with the target molecules in the concentration K3, and determining the binding behavior of the ligands from the ratio of the concentrations K6 and K4, or (E2) determination of the quantities M1 and M2, and calculating a quantity M3 from M2, wherein M3 is a quantity of bound markers in the second mixed phase under the assumption that the markers have been contacted therein in the concentration K2 with the target molecules in the concentration K3, and determining the binding behavior of the ligands from the ratio of the quantities M3 and M1.

In the above method, the markers are present in a native form and the determination of K4 and K5 or M1 and M2 is carried out by mass spectrometry.

In one aspect of the method, in (B) the markers may be present in a concentration K2 and the target molecules may be present in a concentration K3.

In another aspect of the method, the markers GM1 may comprise specifically bound markers SGM1 and the markers GM2 may comprise specifically bound markers SGM2, and SGM1 and SGM2 may be liberated after (D), and the quantities thereof may be used in (E2) instead of M1 and M2.

In yet another aspect, the method may further comprise repeating (A) to (E1) or (A) to (E2) wherein in at least one of (A) and (B) an agent which competes with the markers for a specific binding to the target molecules is added to at least one of the first and second mixed phases in an amount which substantially prevents or cancels a specific binding of the markers to the target molecules.

In another aspect, the method may further comprise repeating (A) to (E1) or (A) to (E2) at least once with a different ratio of K1 and K3.

In a still further aspect of the method of the present invention, (D) may comprise one or more of dialysis, precipitation, adsorption, binding to immobilized molecules which have an affinity to at least one of the target molecules, complexes of the target molecules and the markers and complexes of the target molecules and the ligands, centrifugation, chromatography, and filtration, preferably at least ultrafiltration.

In another aspect of the method, (D) may be carried out under conditions under which at least one of (a) the concentrations of the unbound markers in the first and the second mixed phases and (b) the amounts of the bound markers GM1 and GM2 remain constant.

In yet another aspect of the method, the mass spectrometry may be carried out in one of the MS, MS/MS and MS" modes.

In another aspect, the mass spectrometry may be preceded by at least a capillary electrophoresis, a gas chromatography and/or a liquid chromatography. Preferably, the mass spectrometry is preceded by a FIPLC. The HPLC may comprise reverse phase chromatography.

In another aspect of the method, a sample preparation by means of at least one of extraction, filtration, gas chromatography, capillary electrophoresis, liquid chromatography, FPLC®, reverse phase chromatography, size exclusion chromatography and affinity chromatography may be carried out prior to the mass spectrometry. For example, prior to the mass spectrometry a sample preparation by means of at least one of solid phase extraction, liquid-liquid extraction, ultrafiltration and HPLC may be carried out.

In a still further aspect of the present method, the first and the second mixed phases of (A) and (B) may comprise more than 10 different target molecules and/or more than 10 different markers, for example, more than 100 different target molecules and/or more than 100 different markers. For example, the different markers may differ from each other with respect to one or more of the molar mass, the formation of ions or daughter ions in the mass spectrometry, the chromatographic behavior and the electrophoretic behavior.

In yet another aspect, the first and the second mixed phases of (A) and (B) may comprise a common marker which is specific to different target molecules.

In another aspect, the first mixed phase of (A) may comprises more than 10 different target molecules and/or more than 10 different markers, for example, more than 100 different target molecules and/or more than 100 different markers.

In another aspect of the method, the ligands may have been generated by methods of combinatorial chemistry.

In another aspect, the method may further comprise identifying the ligands which are bound by the target molecules and/or determining the quantity of ligands which are bound by the target molecules. For example, mass spectrometry may be used for identifying the bound ligands and/or for determining the quantity thereof.

In yet another aspect of the method, prior to mass spectrometry the bound ligands may be specifically liberated from the target molecules.

In a still further aspect, the markers may be used as external standard for the determination of K4 and K5 or M1 and M2.

In another aspect of the method, after (D) at least one marker which comprises a marking substance may be added as an internal standard to the first mixed phase and/or the second mixed phase.

In yet another aspect, the target molecules may comprise target molecules that are embedded in membrane structures and/or the target molecules may comprise target molecules that are not bound to a solid support.

In another aspect, the method may further comprise a regeneration of the target molecules after one of (D) and (F2).

In a still further aspect, the target molecules, the markers and/or the ligands may be selected from peptides, proteins, hormones, nucleic acids, sugars, polymers, low molecular weight compounds of natural or synthetic origin and structures on or inside cells, cell fragments, cell homogenates, synaptosomes, liposomes, vesicles, tissue cuts, viruses, components and fragments thereof, capsides, components and fragments thereof, and mixtures of natural substances. For example, at least one of the target molecules, markers and ligands may be selected from receptors, prions, enzymes, transport proteins, ion channels, antibodies, synaptic plasma membrane vesicles and vesicles found inside cells.

The present invention also provides a process for determining the capability of a chemical species to exhibit pharmaceutical activity. This process comprises carrying out the method of the present invention, including the various aspects thereof.

In one aspect of this process, the ligands may comprise the chemical species.

The present invention also provides a new pharmaceutically active species whose capability to exhibit a pharmaceutical activity has been determined by a process which comprises using the method of the present invention, including the various aspects thereof.

(a) preparation of a first mixed phase wherein the ligands in a concentration K1 are contacted with markers, in a concentration K2, which specifically bind to the target molecules, and with the target molecules in a concentration K3, and of a second mixed phase wherein the markers are contacted with the target molecules, wherein after the contacting, the first and second mixed phases are incubated under identical conditions which permit a binding of the ligands and the markers to the target molecules, (b) separation of the bound markers GM1 contained in the first mixed phase from the first mixed phase, and of the bound markers GM2 contained in the second mixed phase from the second mixed phase, and (c1) determination of a concentration K4 of the unbound markers in the first mixed phase, and of a concentration K5 of the unbound markers in the second mixed phase, wherein a concentration K6 is determined from the concentration K5, which concentration K6 corresponds to the concentration of the unbound markers in the second mixed phase under the assumption that the markers in the concentration K2 have been contacted therein with the target molecules in the concentration K3, and determination of the binding behavior of the ligands from the ratio between the concentrations K6 and K4, or (c2) determination of an quantity M1 of the bound markers GM1 and of a quantity M2 of the bound markers GM2, wherein a quantity M3 is determined form the quantity M2, which quantity M3 corresponds to the quantity of the bound markers in the second mixed phase under the assumption that the markers in the concentration K2 have been contacted therein with the target molecules in the concentration K3, and determination of the binding behavior of the ligands from the ratio of the quantities M3 and M1, wherein the markers are present in a native form, and the determination of the concentrations K4 and K5 or of the quantities M2 and M1 is effected by means of mass spectrometry.

The binding behavior is to be construed to mean any behavior which characterizes the specific binding of the ligands to the target molecules at at least one binding site. It may be a relative binding behavior. In this case, the binding behavior indicates whether the ligands bind better or worse than the markers to the target molecules, and optionally, to which extent they bind thereto. It may as well be an absolute binding behavior. In this case, the affinity of the ligands to the target molecules, or the quantity of ligands which are bound to the target molecules are determined. The determination of the binding behavior may as well consist of a mere approximation of the binding behavior.

The term mixed phase comprises both a pure solution and a suspension. The mixed phase may contain membrane structures such as, e.g., vesicles. The target molecules may be present in solution, suspension, immobilized or embedded in membrane structures, in particular, vesicles. Further, instead of the target molecules, the ligands may be immobilized. The target molecules or the ligands may be present immobilized on, e.g., the wall of a vessel or on particles. Further, in the case of target molecules which are embedded in vesicles, the vesicles may be immobilized, e.g., by binding to a solid phase. The conditions according to lit. a are selected so that a binding of the ligands and the markers to the target molecules can take place, in particular, as regards temperature and duration of the incubation. The incubation may be carried out until a binding equilibrium is at least almost reached.

Markers are understood to be known, quantifiable agents which at the employed concentrations K2 and K3 and under the conditions according to lit. a, bind specifically to the target molecules. The binding of the markers to the target molecules is inhibited by the binding of the ligands. This may occur due to, e.g., an allosteric inhibition of the binding, or because the markers and the ligands compete for the binding to the binding site of the ligands on the target molecules. The concentration K6 or the quantity M3, respectively, may be determined by calculation or graphically from the binding properties of the markers and the concentration K5 or the quantity M2, respectively. The concentration K6 is that concentration of unbound marker, and the quantity M3 is that quantity of bound marker, which would be present in the second mixed phase after the incubation if the markers at the concentration K2 had been contacted therein with the target molecules at the concentration K3. From the ratio between the concentrations K6 and K4 or the quantities M3 and M1, respectively, the quantity of the markers whose binding to the target molecules is inhibited, and therefrom the binding behavior of the ligands, may be determined. The ratio in the sense of the invention may be both a relation and a difference. Both the markers and the ligands and the target molecules may be of a uniform type, or may differ from each other.

The separation according to lit. b may take place, for example, by centrifugation of formed complexes. The complexes may contain target molecules and ligands, target molecules and markers, or target molecules, ligands and markers. It is to be understood that instead of a concentration, a quantity, and instead of a quantity, a concentration may be determined.

"Native form" means that the markers do not have any modifications which are necessary for the detection, quantification or identification. Such modifications may, for example, consist in a labeling with a marker substance.

The advantage of the method is that the influence of kinetic differences in the binding behavior between the ligands and the markers on the result can to a large extent be eliminated in that incubation is conducted until a binding equilibrium is at least almost reached. A further advantage of the method according to the present invention is that the target molecules may be present in a native, in particular, not immobilized form. Thereby the method permits to say something about the native binding behavior.

A further advantage of the method is that in the case of ligands which are difficult to quantify directly, only the markers need to be quantified. Thus the method is not subject to limitations which rest in the nature of the ligands and cause problems in the quantification. With respect to the markers, there is the advantage that a development of markers from agents which bind specifically to the target molecules is eliminated, because there is no need for the markers to be labeled. Thus a search for agents which are suitable for labeling by a particular labeling method and bind specifically to the target molecules is not necessary. By the same token, there is no need for a search for agents which bind specifically to the target molecules and which still have a sufficient affinity after the labeling. Moreover, the expenditure which is necessary due to the handling of the utilized marker substances is eliminated, which expenditure may be quite high, in particular, with radioactive marker substances. A health hazard associated with the employment of radioactive marker substances is not present, either.

The use of mass spectrometry is advantageous in that markers which are present in a native form can be detected, quantified and, when different markers are used at the same time, identified.

In the method according to the present invention only the affinity of the markers, and not the affinity of the ligands to be studied, to the target molecules is of relevance. If the markers have a sufficient affinity to the target molecules, the binding behavior of ligands which have very low affinities to the target molecules may be determined by selecting a correspondingly high concentration K1. The utilized markers may be selected so that they can still be detected in low concentrations as well. A further advantage of the method is that an unspecific binding of the ligands to be studied has almost no impact on the result of the measurement. Substantially only the non-specific binding of the markers must be taken into account.

In an advantageous embodiment, in step lit. a the markers in the second mixed phase are contacted in a concentration K2 with the target molecules in a concentration K3. Thereby, the determination of the concentration K6 in step lit. c1 or of the quantity M3 in step lit. c2 is simplified, because under these conditions the concentration K6 is the same as the concentration K5, and the quantity M3 is the same as the quantity M2.

In a further advantageous embodiment, after step lit. b the specifically bound markers SGM1 among the bound markers GM1 and the specifically bound markers SGM2 among the bound markers GM2 are released after the step lit. b. In step lit. c2, the released specifically bound markers SGM1 take the place of the bound markers GM1, and the released specifically bound markers SGM2 take the place of the bound markers GM2. The release may be effected, for example, by adding an excess of molecules which specifically inhibit the binding of the markers. Such molecules may, for example, be competitors which displace the specifically bound markers from the binding site. Another possibility consists in removing by a washing step non-specifically bound markers from the target molecules so that only specifically bound markers remain bonded. The specifically bound markers may then be released by means of non-specific methods. By releasing the specifically bound markers the proportion of non-specifically bound markers, can be taken into account.

Further, for taking into account a non-specific binding of the markers to the target molecules the steps lit. a to c1 or c2 may be carried out an additional time, wherein in step lit. a a material which competes with the markers for the specific binding to the target molecules is added to the first and/or the second mixed phase in such an amount that a specific binding of the markers to the target molecules is largely prevented or terminated. The concentration K4 determined thereby in steps lit. c1 or c2 is identified as K4', K5 as K5' and K6 as K6', and the quantity M1 as M1', M2 as M2' and M3 as M3'. The values determined without the agent are still identified as K4, K5, K6, M1, M2, and M3. The difference between K4' and K4, K5' and K5, and K6' and K6 in each case is the concentration of the specifically bound markers. M1', M2' and M3' each are the quantities of the non-specifically bound markers. The difference between M1 and M1', M2 and M2' and M3 and M3' is the quantity of the specifically bound markers.

In a preferred embodiment of the invention, for the determination of the affinity the steps lit. a to c1 or c2 are carried out at least twice with a different ratio of the concentrations K1 to K3. Preferably, in this case the incubation according to step lit. a is carried out until the binding equilibrium is at least almost reached. From the quantities of the markers whose binding has been inhibited at the different ratio of the concentrations, the affinity can be determined. This can be done by means of a non-linear regression analysis of the competition or displacement graph. The competition or displacement graph represents the inhibition of the binding of the markers by ligands as a function of the concentration of unbound ligands.

Preferably, the separation according lit. b is effected by dialysis, precipitation, adsorption, binding to immobilized molecules which have an affinity to the target molecules or to formed complexes of the target molecules and the markers and/or the ligands, centrifugation, chromatography, or filtration, in particular, ultrafiltration. The separation according to lit b. is preferably carried out under conditions under which the concentration of the unbound markers in the first and in the second mixed phases and/or the quantity of the bound markers GM1 and GM2 remains constant. Any method wherein the separation of bound ligands is carried out under conditions under which the proportions of the bound and the unbound markers and ligands remain constant is suitable for this purpose. As such a method, the separation of formed complexes of target molecules and markers and/or ligands under binding conditions, e.g., by means of centrifugation or filtration, may be contemplated. The advantage of the separation under the mentioned conditions is that a cancellation of a binding equilibrium which is caused by the separation, for example in a washing step, is avoided. A dissociation of the complexes which are formed from the target molecules and the markers and/or the ligands which is caused by the cancellation of the binding equilibrium does not take place. An error in the quantification of the bound ligands resulting therefrom is avoided. A further advantage of the separation under the mentioned conditions is that the first and the second mixed phases do not have to be separated from the bound markers GM1 and GM2 quantitatively. It is sufficient to separate a defined portion of each of the first and the second mixed phases. From this portion and the concentrations K4 and K5 determined in step lit. c1 the amount of marker whose binding has been inhibited by the ligands may be determined.

Advantageously, the mass spectrometry is carried out in the MS, MS/MS or MS" mode. In the MS mode, ions formed by the analyte in the ion source of a mass spectrometer, in the MS/MS mode selectively daughter ions of the ions formed by the analyte, and in the MS" mode selectively further daughter ions of the ions formed by the analyte are quantified. Mass spectrometry may be preceded by a capillary electrophoresis or a gas or liquid chromatography, preferably HPLC, in particular, by using reverse phase chromatography. A separation of molecules which can be distinguished in the mass spectrometry only with difficulty can be achieved thereby. The molecules can then separately be analyzed in the mass spectrometry.

Preferably, prior to the mass spectrometry a sample preparation by means of extraction, preferably solid phase or liquid-liquid extraction, filtration, in particular, ultrafiltration, gas chromatography, capillary electrophoresis, liquid chromatography, preferably HPLC, FPLC®, reverse phase chromatography, size exclusion chromatography and/or affinity chromatography is carried out. Sample preparation means the work-up of a sample from which the concentrations K4 and K5 or the quantities M2 and M1 are to be determined. This may be necessary, for example, if certain components must be removed from the sample. These may be components which are harmful to a mass spectrometer, for example, because they would plug or attack the feed lines, or which reduce the sensitivity of a mass spectrometric measurement, e.g., because they reduce the signal of the marker to be analyzed. Furthermore, these may be components which would interfere with a method which precedes the mass spectrometry.

The first and the second mixed phases according to lit. a may preferably contain more than 10, in particular, more than 100 various target molecules and/or markers. In a preferred embodiment the first and the second mixed phase according to lit. a contain a common marker which is specific to various target molecules. If various markers are used, each marker specifically binds to at least one binding site of a predetermined target molecule. Preferably, the various markers differ from each other at least as regards the molar mass, the formation of ions or daughter ions in the mass spectrometry, or the chromatographic or electrophoretic behavior. Advantageously, the first mixed phase according to lit. a preferably contains more than 10, in particular, more than 100 different ligands. The ligands may have been generated by methods of combinatorial chemistry. Such methods are known, for example, from Felder, E. R., Chimia 48 (1994), 521–541, Gallop et al., J. Med. Chem. 37 (1994), 1233–1251, Houghten, R. A., Trends Genet. 9 (1993), 235–239, Houghten et al., Nature 354 (1991), 84–86, Lam et al., Nature 354 (1991), 82–84, Carell et al., Chem. Biol. 3 (1995), 171–183, Madden et al., Perspectives in Drug Discovery and Design 2 (1994), 269–285, Cwirla et al., Biochemistry 87 (1990), 6378–6382, Brenner, S. and Lerner, R. A., Proc. Natl. Acad. Sci. USA 89 (1992), 5381–5383, Gordon et al., J. Medicinal Chemistry 37 (1994), 1385–1401 and Lebl et al., Biopolymers 37 (1995), 177–198.

By using several different ligands, target molecules and/or markers, the efficiency of the method can be increased significantly. When the method is carried out with different markers, only each of the markers has to be quantified in order to determine if ligands which have an affinity to the target molecules were present in the first mixed phase. Thus the method is suitable for high throughput screening. To find out which of the ligands have an affinity to the target molecules, a deconvolution strategy may be pursued. Here, the method is carried out anew with a reduced number or a different combination of ligands to be studied. By comparing the results it can then be determined which of the ligands has bonded to the target molecules in which amount. Also, the different markers may have different graduated affinities to the target molecules. By determining or approximating the amount of those markers whose binding to the target molecules has been inhibited, the affinity of the ligands to the target molecules may be determined or at least approximated.

In one embodiment, following step lit. c1 or c2 the bound ligands are identified by mass spectrometry and/or the amount of bound ligands is determined by mass spectrometry. For this, the bound ligands may be specifically released prior to mass spectrometry, for example, by the addition of specific competitors. Such a method is very efficient in a high throughput screening in which many substances which predominantly do not bind to the target molecules are studied at the same time with respect to their binding behavior. The identification of the bound ligands or the determination of the quantity of the bound ligands, respectively is necessary only if it results from step lit. c1 or c2 that bound ligands are present at all.

For the determination of the concentrations K4 and K5 or of the quantities M1 and M2 the markers may be used as external standard. Also, it is possible to add to the first and/or the second mixed phase after step lit. b as internal standard at least one marker which has a marking substance. Such an internal standard facilitates the determination of the concentrations K4 and K5 because it is affected to the same extent as the marker itself. Thus, losses in the sample preparation or a possibly necessary concentration of the sample may be taken into account as readily as interfering factors which affect the mass spectrometric determination.

The target molecules may be present embedded in membrane structures. This may be advantageous, for example, with target molecules which are naturally present embedded in membrane structures, and whose binding properties are altered when they are not embedded in membrane structures. In an advantageous embodiment, the target molecules are not bound to a solid support. Thereby a change in the binding behavior of the target molecules by the binding to a solid support and and/or an influence on the kinetics of the binding are avoided.

It is possible to regenerate the target molecules after the steps lit. b or c2 have been carried out. This permits a reuse thereof. This makes sense, in particular, with valuable target molecules, e.g., target molecules on cells on which several studies are to be conducted. The target molecules, markers or ligands may be selected from the following group: peptides, proteins, in particular, receptors, prions, enzymes, transport proteins, ion channels or antibodies, hormones, nucleic acids, sugars, polymers, low molecular weight compounds of natural or synthetic origin and structures on or inside cells, cell fragments, cell homogenates, synaptosomes, liposomes, vesicles, in particular, synaptic plasma membrane vesicles and vesicles which are found in cells, tissue cuts, viruses, their components or fragments of these components, capsides, their components or fragments of these components and mixtures of natural substances.

BRIEF DESCRIPTION OF THE DRAWINGS

In the following, the invention is explained in greater detail by the drawing and by means of working examples. There are shown in FIG. 1 The result of a method carried out according to the present invention, wherein there were employed µ-opioid receptors as target molecules, morphine as a marker and naloxone as a ligand in different concentrations, and FIG. 2 The result of a control experiment wherein there were employed µ-opioid receptors as target molecules, [$^3$H] DAMGO as a marker and naloxone as a ligand.

DETAILED DESCRIPTION OF THE INVENTION

In all working examples, human µ-opioid receptors served as target molecules in the binding assays. The target molecules were provided by means of a membrane preparation of transfected human µ-opioid receptors which express CHO-K1 cells of the company Biotrend, Cologne.

WORKING EXAMPLE 1

Screening of Substance Libraries by Determination of an Unbound Marker 1.1. Binding Assays An assay B0 contained the µ-opioid receptors in a concentration of 5.5 nmol/L, 5 mmol/L of $MgCl_2$ and 50 mmol/L of Tris HCl, pH 7.4, in a total volume of 250 µL. The assay B0 was incubated in a 1.5 ml PP reaction vessel at 25° C. for 150 minutes. Subsequently, the membrane particles were centrifuged off at 50,000 g at 4° C. for 20 minutes. 200 µL were taken from the resultant supernatant Ü0. The following binding assays were treated like B0:

A binding assay B1 which was composed like binding assay B0 and additionally contained 10 nmol/L of morphine as a marker.

A binding assay B2 which was composed like binding assay B1 and additionally contained (±)-methadone in a concentration of 50 µmol/L.

A binding assay B3 which was composed like binding assay B1 and additionally contained the substances of a library 1, consisting of 4-chloroaniline, 2,3-dichloroaniline, methyl benzoate, acetoanilide, amitryptiline, (+)-bicuculine, phenol, naloxone, benzoic acid and tramadol, each in a concentration of 1 µmol/L.

A binding assay B4 which was composed like binding assay B1 and additionally contained the substances of a library 2, each in concentration of 1 µmol/L. The library 2 consists, except for naloxone, of the substances of the library 1.

From B1–B4 supernatants Ü1–Ü4 were recovered.

1.2. Quantification of the Marker

For quantification, a mass spectrometric determination was carried out under the following conditions on an Applied Biosystems API 2000 with TurbolonSpray source in the MRM mode to which a Hewlett Packard HP1100 LC system was coupled:

Column: Supersher 60 RP select B 4 µm 125×2 mm
Eluent: 0.1% HCOOH in water/acetonitrile (80/20)
Flow: 0.4 ml/minute (isocratic)
Sample volume: 20 µL (injected by means of Autosampler)

Morphine was directly measured in the supernatants Ü1–Ü4 at the mass transitions 286.1/115.1 and 286.1/128.1. It was quantified in comparison to morphine which was dissolved in Ü0 in concentrations of 2 nmol/L to 10 nmol/L as external standard. With each sample two measurements were carried out.

1.3. Analysis

In Ü1–Ü4 the following concentrations of unbound morphine were determined as average of two measurements:
Ü1: 2.25 nmol/L
Ü2: 7.66 nmol/L
Ü3: 7.92 nmol/L
Ü4: 2.03 nmol/L From each difference of the employed concentrations of morphine and the concentrations of unbound morphine determined for Ü1–Ü4, the following concentrations of bound morphine were determined for B1–B4:

B1: 7.75 nmol/L
B2: 2.34 nmol/L
B3: 2.08 nmol/L
B4: 7.97 nmol/L

In B1, the binding of morphine was determined without additional competitor as total binding. By contrast, in B2 the binding of morphine was determined in the presence of 50 µmol/L of methadone under conditions which could be expected to approximate a total occupation of the target molecules by methadone. Morphine has merely bound non-specifically in this case. Since in B3 the concentration of bound morphine is only of the order of magnitude of the non-specific binding, there is at least one substance in library 1 which has a significant affinity to the target molecules at a concentration of 1 µmol/L. Since in B4 the concentration of bound morphine is of the order of magnitude of the total binding, there is no substance in library 2 which at a concentration of 1 µmol/L, has a significant affinity to the target molecules. Since the libraries 1 and 2 differ only in that naloxone is contained in library 1, but not in library 2, the affinity exhibiting substance can only be naloxone.

WORKING EXAMPLE 2

Determination of the Affinity of a Ligand by Measurement of the Unbound Marker 2.1. Binding Assays A first binding assay B1 contained the µ-opioid receptors in a concentration of 5.5 nmol/L, 10 nmol/L of morphine as a marker, 5 mmol/L of $MgCl_2$ and 50 mmol/L of Tris HCl, pH 7.4, in a total volume of 250 µL. The binding assay B1 was incubated in a 1.5 ml PP reaction vessel at 25° C. for 150 minutes. Subsequently, the membrane particles were centrifuged off at 50,000 g at 4° C. for 20 minutes. 200 µL were taken from the resultant supernatant Ü1. The following binding assays were treated like B1:

A second binding assay B2 which was composed like binding assay B1 and additionally contained (±)-methadone in a concentration of 50 µmol/L.

Five further binding assays B3–B7 which were composed like B1 and additionally contained naloxone in the following concentrations: B3: 1 nmol/L of naloxone, B4: 10 nmol/L of naloxone, B5: 30 nmol/L of naloxone, B6: 100 nmol/L of naloxone, B7: 1 µmol/L of naloxone.

In a second test series which was carried out in an identical manner, the binding assays B1–B7 were substituted by the identical binding assays B1*–B7*. From B1–B7 the supernatants Ü1–Ü7, and from B1*–B7* the supernatants Ü1* –Ü7* were recovered.

2.2. Quantification of the Marker

The mass spectrometric determination was carried out as described under 1.2. Additionally, naloxone was quantified at the mass transition 328.1/310.1. With each sample two measurements were carried out.

2.3 Analysis

In Ü1–Ü7 and Ü1*–Ü7* the following concentrations of unbound morphine and naloxone were determined as the average of two measurements:

|      | Morphine    | Naloxone    |
| ---- | ----------- | ----------- |
| Ü1:  | 2.25 nmol/L | —           |
| Ü2:  | 7.66 nmol/L | —           |
| Ü3:  | 2.78 nmol/L | 0.35 nmol/L |
| Ü4:  | 4.15 nmol/L | 4.54 nmol/L |
| Ü5:  | 4.75 nmol/L | 15.2 nmol/L |
| Ü6:  | 7.00 nmol/L | 77.2 nmol/L |
| Ü7:  | 8.23 nmol/L | 858 nmol/L  |
| Ü1*: | 2.24 nmol/L | —           |
| Ü2*: | 6.29 nmol/L | —           |
| Ü3*: | 2.18 nmol/L | 0.14 nmol/L |
| Ü4*: | 3.16 nmol/L | 2.96 nmol/L |
| Ü5*: | 4.43 nmol/L | 13.0 nmol/L |
| Ü6*: | 5.50 nmol/L | 61.7 nmol/L |
| Ü7*: | 5.86 nmol/L | 668 nmol/L  |

From each difference of the employed concentrations of morphine and the concentrations of unbound morphine determined for Ü1 –Ü7 and Ü1*–Ü7*, the following concentrations of bound morphine were determined for B1–B7 and B1*–B7*:

| B1: | 7.75 nmol/L | B1*: | 7.76 nmol/L |
| --- | ----------- | ---- | ----------- |
| B2: | 2.34 nmol/L | B2*: | 3.71 nmol/L |
| B3: | 7.22 nmol/L | B3*: | 7.82 nmol/L |
| B4: | 5.85 nmol/L | B4*: | 6.84 nmol/L |
| B5: | 5.15 nmol/L | B5*: | 5.57 nmol/L |
| B6: | 3.00 nmol/L | B6*: | 4.50 nmol/L |
| B7: | 1.77 nmol/L | B7*: | 4.14 nmol/L |

Figure 1:
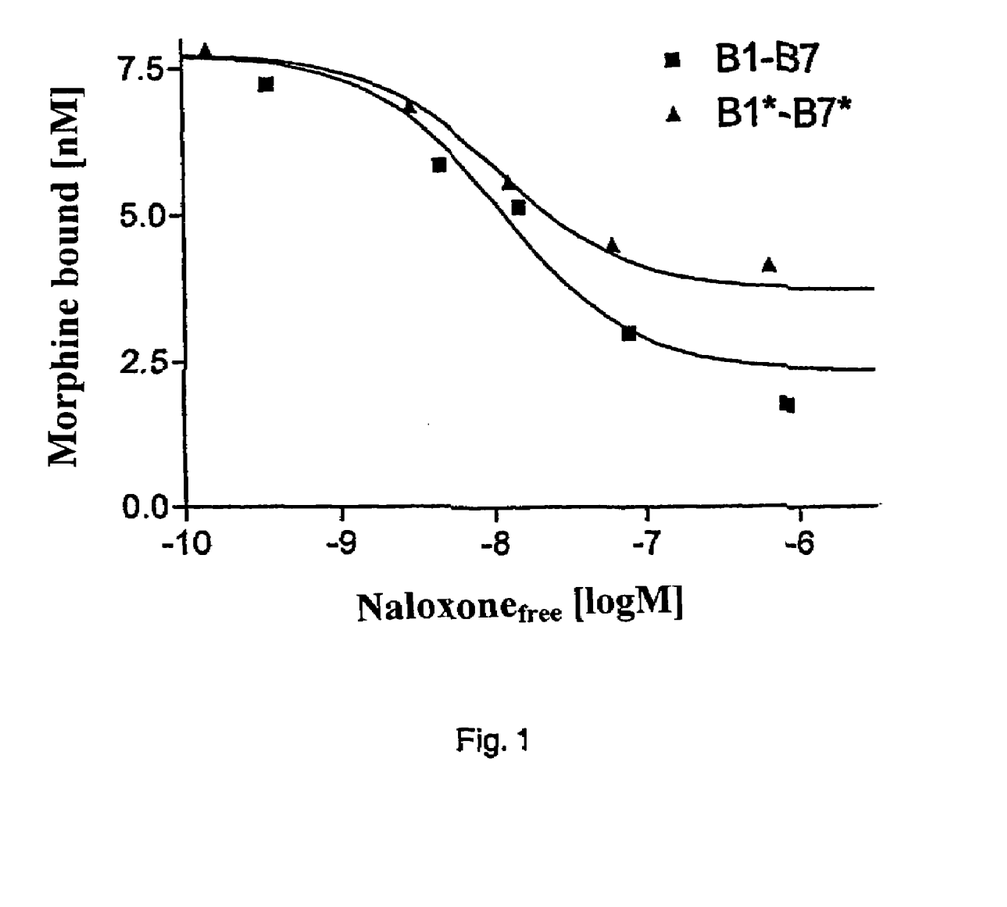

In B1 and B1*, the binding of morphine was determined without additional competitor as total binding. By contrast, in B2 and in B2* the binding of morphine was determined in the presence of 50 µmol/L of methadone under conditions which could be expected to approximate a total occupation of the target molecules by methadone. Morphine has merely bound non-specifically in this case. The specific binding results from the difference of the concentrations determined for B1 and B2 and B1* and B2*, respectively. In FIG. 1 the concentration of the bound morphine is represented as a function of the concentration of the unbound, i.e., free naloxone.

By means of a non-linear regression analysis carried out with the program Prism 2.01 Graph Pad, San Diego, USA, the concentration of free naloxone at which 50% of the morphine are specifically bound was determined. This value is called $IC_{50}$ value. For the binding assays B1–B7, an $IC_{50}$ value of 11.9 nmol/L, and for the binding assays B1*–B7*, an $IC_{50}$ value of 11.6 nmol/L was determined.

The $K_i$ value as a measure of the affinity of naloxone to the target molecules may be determined as follows according to Hulme, E. C. and Birdsall, N. J. M., Strategy and tactics in receptor-binding studies in Receptor-Ligand-Interactions, ed. Hulme, E. C., Oxford University Presss, Oxford (1992), 63–176, in binding experiments in which the concentration of the free marker is different to a non-negligible extent from the starting concentration of the marker:

$$K_i = \frac{IC_{50}}{2\frac{(L^* - L_0^*)}{L_0^*} + 1 + \frac{L^*}{K_d}}$$

The meanings are:

$L^*$: Concentration of the marker at the $IC_{50}$ value.
$L_0^*$: Concentration of the free marker in the absence of the competitor and $K_d$: Affinity of the marker to the target molecules.

From Raynor, K., Kong, H., Mestek, A., Bye, L. S., Tian, M., Liu, J., Yu, L., and Reisine, T., Characterisation of the cloned Mu opioid Receptor, J. Pharmacol. Exp. Ther. 272 (1995), 423–428, it is known that the $K_d$ value for morphine is 2.0 nmol/L. From this, there results for B1–B7 at
$IC_{50}$=11.9 nmol/L
L*=4.8 nmol/L
$L_0$*=2.25 nmol/L a $K_i$ for naloxone of 1.4 nmol/L with respect to the human µ-opioid receptors.

For B1 *–B7*, there results at
$IC_{50}$=11.6 nmol/L
L*=4.2 nmol/L
$L_0$*=2.24 nmol/L a $K_i$ for naloxone of 1.7 nmol/L with respect to the human µ-opioid receptors.

2.4. Control Experiment

Competition Naloxone/[$^3$H]DAMGO on Human µ-Opioid Receptors

Figure 2:
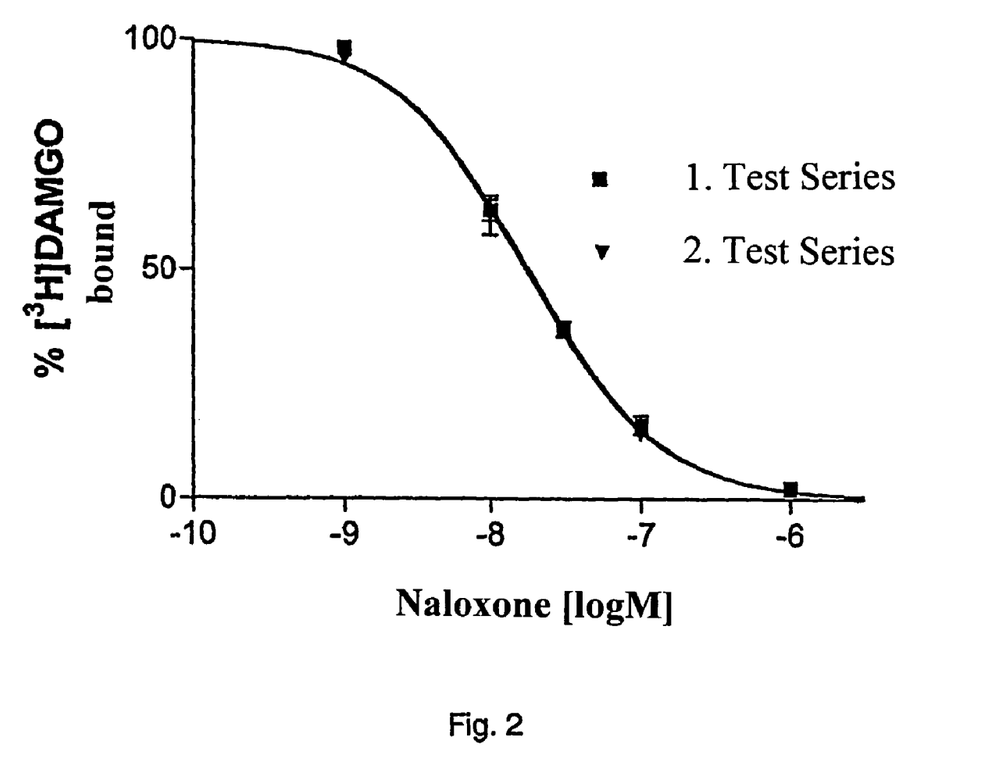

[$^3$H]DAMGO is the $^3$H labeled µ-opioid receptor agonist Tyr-D-Ala-Gly-N-Methyl-Phe-Gly(ol)-encephaline. 22 µg of protein of a membrane preparation of transfected CHO K1 cells of the company Biotrend, Cologne, which preparation contained 30 fmol of human µ-opioid receptors, were incubated as described in Wanner, K. T., Praschak, I., Höfner, G. and Beer, H., Asymmetric Synthesis and Enantiospecificity of Binding of 2-(1,2,3,4-Tetrahydro-1-isoquinolinyl)-ethanol derivatives to µ- and κ-receptors, Arch. Pharm. 329 (1996), 11–12, with 4.5 nmol/L of [$^3$H]DAMGO and 0 nmol/L, 1 nmol/L, 10 nmol/L, 30 nmol/L, 100 nmol/L and 1 µmol/L of naloxone for 60 minutes at 25° C. in a total volume of 250 µL. The non-specific binding was determined in the presence of 50 µmol/L of (±)-methadone. Two test series were carried out in triplicate each. In FIG. 2 the concentration of the formed [$^3$H]DAMGO is represented as a function of the concentration of the naloxone employed. By means of a non-linear regression analysis carried out with the program Prism 2.01 Graph Pad, San Diego, USA, the $IC_{50}$ value, i.e., the concentration of naloxone at which 50% of the [$^3$H]DAMGO are specifically bound was determined. From Raynor, K., Kong, H., Mestek, A., Bye, L. S., Tian, M., Liu, J., Yu, L., and Reisine, T., Characterisation of the cloned Mu opioid Receptor, J. Pharmacol. Exp. Ther. 272 (1995), 423–428, it is known that the Kd value for DAMGO is 1.4 nmol/L. According to Cheng, Y. C. and Prusoff, W. H., Relationship between the inhibition constant Ki and the concentration of inhibitor which causes 50 cent inhibition IC50 of an enzymatic reaction, Biochem. Pharmacol. 22 (1973), 3099–3108, the following $K_i$ values of naloxone with respect to human µ-opioid receptors were calculated from the $K_d$-value for DAMGO and the $IC_{50}$ values of 18 nmol/L and 17 nmol/L from the first and second test series, respectively:
1st Test series $K_i$=4.2 nmol/L
2nd Test series $K_i$=4.1 nmol/L

WORKING EXAMPLE 3

Screening of Substance Libraries By Measuring the Bound Marker After Its Controlled Release 3.1. Binding Assays The binding assays B1–B4 described in Working Example 1 were used and treated as described under 1.1. Pellets P1–P4 obtained from B1–B4 after centrifugation were treated as follows: P1–P4 were each washed three times with 200 µL of 5 mmol/L of $MgCl_2$ and 50 mmol/L of Tris HCl, pH 7.4. Subsequently, P1–P4 were each resuspended in 200 µL of 5 mmol/L of $MgCl_2$ and 50 mmol/L of Tris HCLl, pH 7.4, and incubated for 15 minutes at room temperature in a shaking water bath and centrifuged at 50,000×g for 20 minutes at 4° C. The resultant supernatants were discarded and the obtained pellets P1'–P4' were each resuspended with 200 µL of 50 µnmol/L of (±)-methadone in 5 mmol/L of $MgCl_2$ and 50 mmol/L of Tris HCl, pH 7.4 and once again incubated as before for 15 minutes. The assays were subsequently centrifuged as before, whereby the supernatants F1–F4 were recovered.

3.2. Quantification of the Marker

The morphine contained in F1–F4 was quantified as described under 1.2.

3.3. Analysis

In F1–F4 the following concentrations of unbound, i.e., released morphine were measured as average of two measurements:
F1: 4.84 nmol/L
F4: 4.80 nmol/L
F2/F3: morphine not detectable In B1, the binding of morphine was determined without additional competitor as total binding. By contrast, in B2 the binding of morphine was determined in the presence of 50 µmol/L of methadone under conditions which could be expected to approximate a total occupation of the target molecules by methadone. Morphine has merely bound non-specifically in this case. From P2' apparently no morphine could be released, since morphine is not detectable in F2. Accordingly, it can be assumed that the morphine which was detected in F1 and released from P1' was bound specifically. Since about as much morphine was released from P4' in F4 as from P1' into F1, the library 2 apparently does not contain a ligand with pronounced affinity to the target molecules. Apparently no morphine could be released from P3', because morphine was not detectable in F3. Accordingly, the library 1 contains at least one substance which has a significant affinity to the target molecules at a concentration of 1 µmol/L. Since the libraries 1 and 2 differ only in that naloxone is contained in library 1, but not in library 2, the substance with affinity can only be naloxone.

WORKING EXAMPLE 4

Screening of Substance Libraries By Measuring the Unbound Marker and Subsequent Identification of Ligands Having Affinity Following Their Controlled Release 4.1. Binding Assays With the exception of each containing the substances of the library 1 and of the library 2 in a concentration of 10 nmol/L instead of 1 µnmol/L, the binding assays B1#–B4# were the same as the binding assays B1–B4 in Working Example 1. The binding assays were treated as described under 1.1. By centrifugation, supernatants Ü1#–Ü4# and pellets P1#–P4# were obtained from the binding assays B1#–B4#. P4# was discarded. P1#–P3# were each washed three times with 200 µL of 5 mmol/L of $MgCl_2$ and 50 mmol/L of Tris HCl, pH 7.4. Subsequently, P1#–P3# were each resuspended in 200 µL of 5 mmol/L of $MgCl_2$ and 50 mmol/L of Tris HCl, pH 7.4, incubated for 15 minutes at room temperature in a shaking water bath, and centrifuged at 50,000× g for 20 minutes at 4° C. The resultant supernatants were discarded and the obtained pellets P1#'–P3#' were each resuspended with 200 µL of 50 µmol/L of (±)-methadone in 5 mmol/L of $MgCl_2$ and 50 mmol/L of Tris HCl, pH 7.4, and once again incubated as before for 15 minutes. The assays were subsequently centrifuged as before, whereby the supernatants F1#–F3# were recovered.

4.2 Quantification of the Ligands

Unbound or free morphine, respectively, was quantified in Ü1#–Ü4# and in F1#–F3# as described under 1.2. In F3#, also the individual substances of the library 1 were additionally determined at the respective specific mass transitions. However, except for naloxone, none of the substances could be detected in F3#. The released naloxone was quantified at the mass transition 328.1/310.1. Two measurements were carried out with each sample.

4.3. Analysis

In Ü1#–Ü4# the following concentrations of unbound morphine were determined as mean values:
Ü1#: 2.39 nmol/L
Ü2#: 7.80 nmol/L
Ü3#: 5.02 nmol/L
Ü4#: 2.76 nmol/L Since B4# from the library 2 apparently did not contain a ligand with significant affinity to the target molecules, P4# was discarded.

In F1#–F3# the following average concentrations of released morphine and naloxone were determined:

|  | Naloxone | Morphine |
| --- | --- | --- |
| F1: |  | 4.63 nmol/L |
| F2: |  | morphine not detectable |
| F3: | 2.30 nmol/L | 2.93 nmol/L |

In F3#, naloxone and morphine could be detected in approximately the same concentrations. Apparently, among the substances of library 1 only naloxone has high affinity to the target molecule, while the remaining substances have a distinctly lower affinity. Since the identified ligand naloxone and the marker morphine were contained in binding assay B3# in the same concentrations, it can be inferred that the released identified ligand naloxone has an affinity to target molecules which is in the range of the affinity of the marker morphine.

WORKING EXAMPLE 5

Screening of Test Sustances with Regard to Their Affinity to Different Target Molecules in Native Materials by Simultaneously Determining the Unbound Portions of Two Different Markers 5.1. Conception SCH23390 and spiroperidol possess high affinity to $D_1$- and $D_2$-type receptors in the central nervous system, and are used as markers for the respective target molecules. As native material which contains both $D_1$ and $D_2$ receptors in sufficient amount, a membrane fraction from the striatum of the porcine brain is employed. Test substances are simultaneously examined in a binding assay with respect to their ability to inhibit the specific binding of SCH23390 to $D_1$ receptors or the specific binding of spiroperidol to $D_2$ receptors, respectively.

5.2. Recovery of the Receptor Material

The striata of 20 porcine brains (raw mass 20 g) were homogenized with a Potter in the ten-fold volume of 0.32 mol/L of sucrose, and were centrifuged at 1,000 g for 10 min at 4° C. The supernatant was centrifuged at 20,000 g for 10 min at 4° C. The pellets were resuspended in 50 mmol/L of Tris HCl, pH 7.4 (buffer), and centrifuged at 30,000 g for 10 min at 4° C. The last step was repeated. The resultant membrane fraction was frozen in liquid $N_2$.

5.3. Binding Assays

In a first binding assay (B1), an aliquot of the membrane fraction which contained 1.7 mg of protein was incubated with 20 nmol/L of each of SCH23390 and spiroperidol in 50 mmol/L of Tris HCl, pH 7.4 in a total volume of 250 µL for 40 min at 25° C. in a 1.5 ml PP reaction vessel. Subsequently, the membrane particles were centrifuged off at 50,000×g for 20 min at 4° C. 200 µL of the supernatant (Ü1) were taken off.

A second binding assay (B2) which additionally contained butaclamol at a concentration of 100 µmol/L was carried out analogously to B1 and afforded Ü2. A third binding assay (B3) which additionally contained haloperidol as a test substance at a concentration of 1 µmol/L was carried out analogously to B1 and afforded Ü3. A fourth binding assay (B4) which additionally contained chlorpromazine as a test substance at a concentration of 1 µmol/L was carried out analogously to B1 and afforded Ü4. A fifth binding assay (B5) which additionally contained methyl benzoate as a test substance at a concentration of 1 µmol/L was carried out analogously to B1 and afforded Ü5. All binding assays B1 to B5 were carried out as double determinations.

A further supernatant Ü0 which contained neither SCH23390 nor spiroperidol during the incubation was recovered in analogous manner.

5.4. Quantification of the Marker

The mass spectroscopic determination of the marker was carried out on an Applied Biosystems API 2000 with TurbolonSpray source in the MRM mode, to which a Hewlett Packard HP1100 LC system was coupled. The markers SCH23390 and spiroperidol were measured directly side by side in the supernatants Ü1–Ü5 by means of the MRM method which was based on the mass transitions of 288.1/91.1 for SCH23390 and 395.9/122.9 for spiroperidol, respectively, and were quantified in comparison to external standards (1 nmol/L to 5 nmol/L of SCH23390 and spiroperidol in Ü0). All samples were measured twice.

Column: Superspher 60 RP select B 4 µm 125×2 mm with 10×2 mm pre-column
Eluent: 0.1% HCOOH in water/acetonitrile (65/35)
Flow: 0.35 ml/minute (isocratic)
Sample volume: 20 µL (injected by means of Autosampler)

5.5. Analysis

In Ü1–Ü5 the following concentrations of unbound markers were determined (average values of doubles and double LCMS determination):

|  | SCH23390 | Spiroperidol |
| --- | --- | --- |
| Ü1: | 2.88 nmol/L | 1.93 nmol/L |
| Ü2: | 4.15 nmol/L | 2.75 nmol/L |

-continued

|     | SCH23390    | Spiroperidol |
|-----|-------------|--------------|
| Ü3: | 2.77 nmol/L | 2.78 nmol/L  |
| Ü4: | 2.71 nmol/L | 2.29 nmol/L  |
| Ü5: | 2.71 nmol/L | 1.89 nmol/L  |

Each of the differences of the markers in Ü1 and Ü2 describes the specific binding for SCH23390 and spiroperidol (for SCH23390 1.27 nmol/L; for spiroperidol 0.82 mnol/L).

Among the studied test substances (haloperidol, chlorpromazine and methyl benzoate), none is capable, at the employed concentration of 1 μmol/L, to inhibit the specific binding of the marker SCH23390 to $D_1$-type receptors. Apparently, none of the studied test substances exhibits (in the concentration employed) affinity to $D_1$-type receptors.

In the employed concentration of 1 μmol/L, methyl benzoate is not capable of inhibiting the specific binding of spiroperidol to $D_2$-type receptors. Apparently, methyl benzoate exhibits (in the concentration employed) no affinity to $D_2$-type receptors. Haloperidol completely inhibits the specific binding of the marker spiroperidol to $D_2$-type receptors, while chlorpromazine inhibits the specific binding of the marker spiroperidol to $D_2$-type receptors only at about 50%. Apparently, haloperidol has a higher affinity to $D_2$-type receptors than chlorpromazine.

What is claimed is:

1. A method for determining the binding behavior of ligands which bind specifically to target molecules at at least one binding site, which method comprises:
    (A) preparing a first mixed phase wherein the ligands are contacted with (i) markers which bind specifically to the target molecules, and (ii) with the target molecules, wherein the ligands are present in a concentration K1, the markers are present in a concentration K2 and the target molecules are present in a concentration K3;
    (B) preparing a second mixed phase wherein the markers are contacted with the target molecules;
    (C) incubating the first and second mixed phases under identical conditions, which conditions permit a binding of the ligands and the markers to the target molecules, resulting in (a) a quantity M1 of markers GM1 that are bound to target molecules and a concentration K4 of unbound markers in the first mixed phase and (b) a quantity M2 of markers GM2 that are bound to target molecules and a concentration K5 of unbound markers in the second mixed phase;
    (D) separating the markers GM1 from the first mixed phase and separating the markers GM2 from the second mixed phase;
    (E1) determination of the concentrations K4 and KS, and calculating a concentration K6 from K5, wherein K6 is a concentration of unbound markers in the second mixed phase under the assumption that the markers have been contacted therein in the concentration K2 with the target molecules in the concentration K3, and determining the binding behavior of the ligands from the ratio of the concentrations K6 and K4, or
    (E2) determination of the quantities M1 and M2, and calculating a quantity M3 from M2, wherein M3 is a quantity of bound markers in the second mixed phase under the assumption that the markers have been contacted therein in the concentration K2 with the target molecules in the concentration K3, and determining the binding behavior of the ligands from the ratio of the quantities M3 and M1 ;
    wherein the markers are present in a native form and the determination of K4 and K5 or M1 and M2 is carried out by mass spectrometry.

2. The method of claim 1, wherein in (B) the markers are present in a concentration K2 and the target molecules are present in a concentration K3.

3. The method of claim 1, wherein the markers GM1 comprise specifically bound markers SGM1 and the markers GM2 comprise specifically bound markers SGM2 and wherein SGM1 and SGM2 are liberated after (D), and quantities thereof are used in (E2) instead of M1 and M2.

4. The method of claim 1, further comprising repeating (A) to (E1) or (A) to (E2) wherein in at least one of (A) and (B) an agent which competes with the markers for a specific binding to the target molecules is added to at least one of the first and second mixed phases in an amount which substantially prevents or cancels a specific binding of the markers to the target molecules.

5. The method claim 1, further comprising repeating (A) to (E1) or (A) to (E2) at least once with a different ratio of K1 and K3.

6. The method of claim 1, wherein (D) comprises at least one of dialysis, precipitation, adsorption, binding to immobilized molecules which have an affinity to at least one of the target molecules, complexes of the target molecules and the markers and complexes of the target molecules and the ligands, centrifugation, chromatography, and filtration.

7. The method of claim 1, wherein (D) comprises ultrafiltration.

8. The method of claim 1 , wherein (D) is carried out under conditions under which at least one of (a) the concentrations of the unbound markers in the first and the second mixed phases and (b) the amounts of the bound markers GM 1 and GM2 remain constant.

9. The method of claim 1, wherein the mass spectrometry is carried out in one of the MS, MS/MS and MS$^n$ modes.

10. The method of claim 9, wherein the mass spectrometry is preceded by at least one of a capillary electrophoresis, a gas chromatography and a liquid chromatography.

11. The method of claim 1, wherein the mass spectrometry is preceded by a HPLC.

12. The method of claim 11, wherein the HPLC comprises reverse phase chromatography.

13. The method of claim 1, wherein prior to the mass spectrometry a sample preparation by means of at least one of extraction, filtration, gas chromatography, capillary electrophoresis, liquid chromatography, fast preformance liquid chromatography, reverse phase chromatography, size exclusion chromatography and affinity chromatography is carried out.

14. The method of claim 1, wherein prior to the mass spectrometry a sample preparation by means of at least one of solid phase extraction, liquid-liquid extraction, ultrafiltration and HPLC is carried out.

15. The method of claim 1, wherein the first and the second mixed phases of (A) and (B) comprise at least one of more than 10 different target molecules and more than 10 different markers.

16. The method of claim 15, wherein the first and the second mixed phases of (A) and (B) comprise at least one of more than 100 different target molecules and more than 100 different markers.

17. The method of claim 1, wherein the first and the second mixed phases of (A) and (B) comprise a common marker which is specific to different target molecules.

18. The method of claim 15, wherein the different markers differ from each other with respect to at least one of the molar mass, the formation of ions or daughter ions in the mass spectrometry, the chromatographic behavior and the electrophoretic behavior.

19. The method of claim 1, wherein the first mixed phase of (A) comprises at least one of more than 10 different target molecules and more than 10 different markers.

20. The method of claim 19, wherein the first mixed phase of (A) comprises at least one of more than 100 different target molecules and more than 100 different markers.

21. The method of claim 19, wherein the ligands are generated by methods of combinatorial chemistry.

22. The method of claim 1, further comprising at least one of identifying ligands which are bound by the target molecules and determining a quantity of ligands which are bound by the target molecules.

23. The method of claim 22, wherein mass spectrometry is used for the at least one of identifying the bound ligands and determining the quantity thereof.

24. The method of claim 23, wherein prior to mass spectrometry the bound ligands are specifically liberated from the target molecules.

25. The method of claim 1, wherein the markers are used as external standard for the determination of K4 and KS or M1 and M2.

26. The method of claim 1, wherein after (D) at least one marker which comprises a marking substance is added as an internal standard to at least one the first and second mixed phases.

27. The method of claim 1, wherein the target molecules comprise target molecules that are embedded in membrane structures.

28. The method of claim 1, wherein the target molecules comprise target molecules that are not bound to a solid support.

29. The method of claim 1, further comprising a regeneration of the target molecules after one of (D) and (F2).

30. The method of claim 1, wherein at least one of the target molecules, markers and ligands are selected from peptides, proteins, hormones, nucleic acids, sugars, polymers, low molecular weight compounds of natural or synthetic origin and structures on or inside cells, cell fragments, cell homogenates, synaptosomes, liposomes, vesicles, tissue cuts, viruses, components and fragments thereof, capsides, components and fragments thereof, and mixtures of natural substances.

31. The method of claim 30, wherein at least one of the target molecules, markers and ligands are selected from receptors, prions, enzymes, transport proteins, ion channels, antibodies, synaptic plasma membrane vesicles and vesicles found inside cells.

32. A process for determining the capability of a chemical species to exhibit pharmaceutical activity, wherein the process comprises carrying out the method of claim 1.

33. The process of claim 32, wherein the ligands comprise the chemical species.

* * * * *